US005523808A

United States Patent [19]
Kohayakawa

[11] Patent Number: 5,523,808
[45] Date of Patent: Jun. 4, 1996

[54] OPHTHALMIC APPARATUS HAVING AN INTRAOCULAR PRESSURE MEASURING SYSTEM

[75] Inventor: Yoshimi Kohayakawa, Yokohama, Japan

[73] Assignee: Canon Kabushiki Kaisha, Tokyo, Japan

[21] Appl. No.: 337,143

[22] Filed: Nov. 10, 1994

Related U.S. Application Data

[63] Continuation of Ser. No. 293, Jan. 4, 1993, abandoned.

[30] Foreign Application Priority Data

Jan. 8, 1992 [JP] Japan .................. 4-20421
Jun. 5, 1992 [JP] Japan .................. 4-169912
Dec. 29, 1992 [JP] Japan .................. 4-360640

[51] Int. Cl.$^6$ .................. A61B 3/14
[52] U.S. Cl. .................. 351/210; 351/209; 125/648
[58] Field of Search .................. 351/209, 210, 351/211, 212, 247; 128/645, 648, 652; 354/62

[56] References Cited

U.S. PATENT DOCUMENTS

| | | |
|---|---|---|
| 4,697,895 | 10/1987 | Sekiguchi et al. . |
| 4,704,012 | 11/1987 | Kohayakawa . |
| 4,817,620 | 4/1989 | Katsuragi et al. ............ 128/648 |
| 4,820,037 | 4/1989 | Kohayakawa et al. . |
| 4,825,873 | 5/1989 | Kohayakawa . |
| 4,991,584 | 2/1991 | Kobayashi et al. ............ 128/648 |
| 5,031,623 | 7/1991 | Kohayakawa et al. . |
| 5,037,194 | 8/1991 | Kohayakawa . |
| 5,107,851 | 4/1992 | Yano et al. ............ 128/648 |
| 5,144,346 | 9/1992 | Nakamura et al. . |

Primary Examiner—William L. Sikes
Assistant Examiner—Hung Xuan Dang
Attorney, Agent, or Firm—Fitzpatrick, Cella, Harper & Scinto

[57] ABSTRACT

A composite ophthalmic apparatus includes an intraocular pressure measuring system for spraying a fluid from a nozzle against an eye to be examined to deform its cornea and detecting a deformation amount of the cornea to measure the intraocular pressure of the eye, and another ophthalmic optical system. The apparatus is provided with a system for displacing the nozzle or the ophthalmic optical system relative to an eye to be examined so as to allow the center of the nozzle or the optical axis of the ophthalmic optical system to agree with the visual axis of the eye to be examined.

14 Claims, 12 Drawing Sheets

FIG. 7
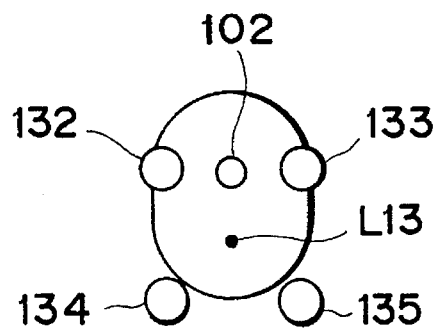
FIG. 8A    FIG. 8B    FIG. 8C
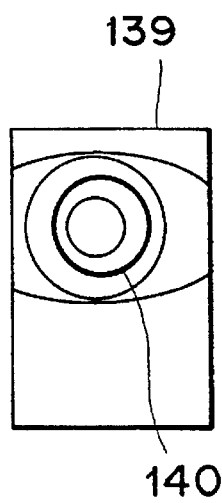 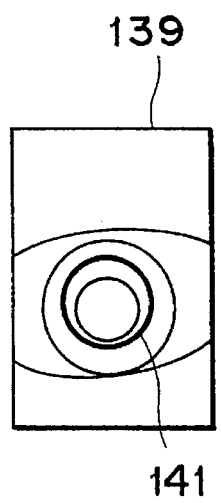 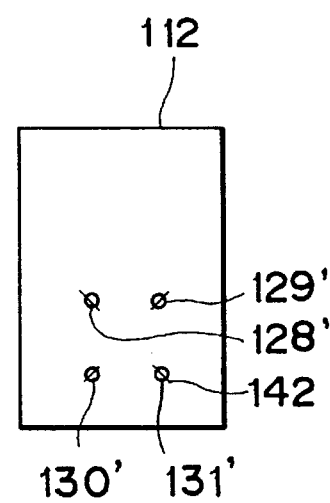

OPHTHALMIC APPARATUS HAVING AN INTRAOCULAR PRESSURE MEASURING SYSTEM

This application is a continuation of application Ser. No. 08/000,293 filed Jan. 4, 1993 now abandoned.

BACKGROUND OF THE INVENTION

1. Field of the Invention

The present invention relates to an ophthalmological apparatus for use in ophthalmic hospitals and the like, such as a noncontact tonometer for spraying air from a nozzle against a cornea to detect its deformation, thereby obtaining the intraocular pressure, of the eye or a composite ophthalmic apparatus obtained by combining the noncontact tonometer with another eye examining apparatus.

2. Related Background Art

Conventionally, composite ophthalmic apparatuses obtained by combining an air spraying type noncontact tonometer with, e.g., an eye refractometer, an eye fundus camera, or a slit lamp, have been proposed.

In these conventional apparatuses, however, a moving part for switching the individual eye examining apparatuses is enlarged and complicated in structure. In addition, these composite apparatuses are not necessarily preferable in their functions and operabilities. In particular, since the air spraying direction in these apparatuses is in agreement with the direction of the visual axis of an eye to be examined, it is difficult to combine the tonometer with another optical instrument or to reduce the dimensions of the entire apparatus. Furthermore, if an anterior eye observation device for aligning an eye to be examined with the composite apparatus is to be incorporated in the apparatus, there is the possibility that the apparatus is further complicated in structure.

SUMMARY OF THE INVENTION

It is an object of the present invention to solve the above problems and to provide a tonometer or an ophthalmological apparatus with a high degree of freedom in design, which is a combination of, e.g., an intraocular pressure measurement apparatus with another apparatus, and which is neither enlarged by a moving part nor degraded in operability and function.

It is a principal object of the present invention to provide an ophthalmological apparatus obtained by combining an intraocular pressure measurement apparatus with another eye examining apparatus and an anterior eye observation device usable in aligning an eye to be examined with the apparatus, which can minimize the increase in dimensions of the entire apparatus and is not degraded in operability and functions.

Other objects of the present invention will become apparent in the description of embodiments of the present invention to be presented later.

BRIEF DESCRIPTION OF THE DRAWINGS

FIG. 7 is a front view showing the pressurizing measuring means;

FIGS. 8A, 8B, and 8C are views for explaining the measurement operation;

DESCRIPTION OF THE PREFERRED EMBODIMENTS

In a composite ophthalmic apparatus having an intraocular pressure measuring means spraying a fluid from a nozzle against an eye to be examined to deform its cornea and detecting deformation of the cornea to measure the intraocular pressure of the eye, and another ophthalmic means, the ophthalmic apparatus according to the embodiments of the present invention to be described below is characterized by comprising a means for displacing the nozzle or the ophthalmic optical means relative to an eye to be examined so as to allow the center of the nozzle or the optical axis of the ophthalmic optical means to agree with the visual axis of the eye to be examined.

The composite ophthalmic apparatus with the above arrangement has a nozzle at a position between an eye to be examined and the intraocular pressure measuring optical means and other ophthalmic optical means such that the nozzle is displaceable at that position.

Embodiments of the present invention will be described in detail below with reference to the accompanying drawings.

Figure 1:
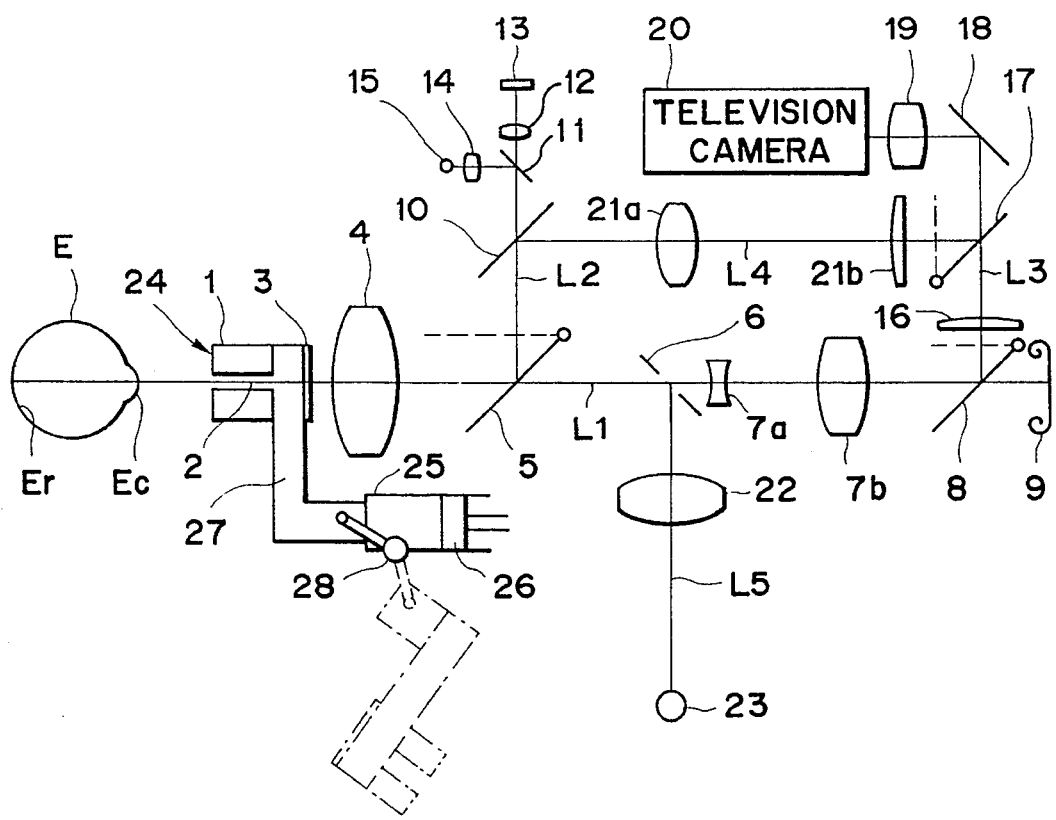
FIG. 1 is a schematic view showing the arrangement of the first embodiment of the present invention.

FIG. 1 is a schematic view showing an apparatus according to the first embodiment of the present invention, which is a combination of a tonometer and an eye fundus camera. In an optical path L1 along the direction of the visual axis of an eye E to be examined, a nozzle 2 held by an optical holding member 1 consisting of a light-transmitting material, a window member 3, an objective lens 4, a movable mirror 5, a perforated mirror 6, imaging lenses 7a and 7b, a quick return mirror 8, and a film 9 are arranged in this order from the side of the eye E to be examined. In an optical path L2 along the reflection direction of the movable mirror 5 when the movable mirror 5 is set obliquely in the optical path (i.e., the optical axis; this will be the same hereinafter) L1, a dichroic mirror 10, a half mirror 11, a lens 12, and a photodetector 13 are arranged. A lens 14 and a measurement light source 15 are provided in the reflection direction of the half mirror 11. In an optical path L3 along the reflection direction of the quick return mirror 8 when the quick return mirror 8 is inserted into the optical path L1, a lens 16, a movable mirror 17, a mirror 18, a lens 19, and a television camera 20 are disposed. In addition, in an optical path L4 between the dichroic mirror 10 and the movable mirror 17, lenses 21a and 21b are interposed. Also, in an optical path L5 along the incident direction of the perforated mirror 6, a lens 22 and a light source 23 are placed. Note that when this ophthalmic apparatus is used as an eye fundus camera and photographing is performed, the movable mirrors 5 and 17 are moved to positions indicated by broken lines.

In a pressurizing measurement unit 24 of a tonometer, which includes the nozzle 2 and the window member 3, air in a cylinder 25 is compressed by a piston 26 and sprayed from the nozzle 2 through a fluid passage 27. The entire pressurizing measurement unit 24 is manually or electrically pivoted about a pivot 28 so as to be inserted into or removed from the optical path L1 in accordance with the application purpose of the ophthalmic apparatus.

In order to use the ophthalmic apparatus having the above arrangement as a tonometer, an infrared light beam emitted from the measurement light source 15 through the lens 14 is reflected by the half mirror 11, the dichroic mirror 10, and the movable mirror 5 at a position indicated by a solid line, and projected onto a cornea Ec of the eye E to be examined through the objective lens 4, the window member 3, and the nozzle 2 in the optical path L1. The light beam reflected by the cornea Ec returns through the same light paths L1 and L2 and is received by the photodetector 13 through the half mirror 11 and the lens 12.

In this condition, when air is sprayed from the nozzle 2 against the cornea Ec, the cornea Ec becomes applanate under pressure to produce a predetermined change in curvature, and the position of a reflected image obtained by the cornea Ec also changes in the direction of optical axis accordingly. Therefore, by determining a predetermined deformation amount and placing the photodetector 13 at a position where the position of the photodetector 13 becomes conjugate to the light source via the cornea Ec having this deformation amount, it is possible to detect the predetermined deformation, when the output from the photodetector 13 becomes maximum. Therefore, by measuring the pressure in the cylinder 25 at that time by using a pressure measuring means, the intraocular pressure can be detected in accordance with a known conventional technique.

In order to use this embodiment for relative positioning between the eye and the apparatus, a light beam reflected by an anterior part of the eye returns to the optical path L2 through the same optical path L1 and is reflected by the dichroic mirror 10. The reflected light beam is imaged on the television camera 20 via the lenses 21a and 21b, the movable mirror 17, the mirror 18, and the lens 19, so that the operator performs relative positioning between the eye and the apparatus by observing the image on a television monitor (not shown).

In order to use this embodiment as an eye fundus camera, the pressurizing measurement unit 24 is removed from the optical path L1 to the position indicated by a broken line in FIG. 1 by pivoting it about the pivot 28. And when photographing is performed, the movable mirrors 5 and 17 are also moved to the positions indicated by the broken lines in FIG. 1.

In the case of an eye fundus camera, a light beam from the light source 23 via the lens 22, the perforated mirror 6, and the objective lens 4 illuminates an eye fundus Er of the eye E to be examined, and the resultant eye fundus image returns through the optical path L1 and is imaged on the television camera 20 via the objective lens 4, the perforated mirror 6, the lenses 7a and 7b, the quick return mirror 8, the lens 16, the mirror 18, and the lens 19. The operator performs the relative positioning while observing this image of the eye fundus on the television monitor, moves the quick return mirror 8 to the position indicated by the broken line, and photographs the image of the eye fundus Er on the film 9.

In this embodiment, a moving part for combining the individual ophthalmic apparatuses is only the mechanism for inserting/removing the pressurizing measurement unit 24 in the one-dimensional vertical direction. Therefore, the structure is simple so as not to enlarge the entire apparatus.

Figure 2:
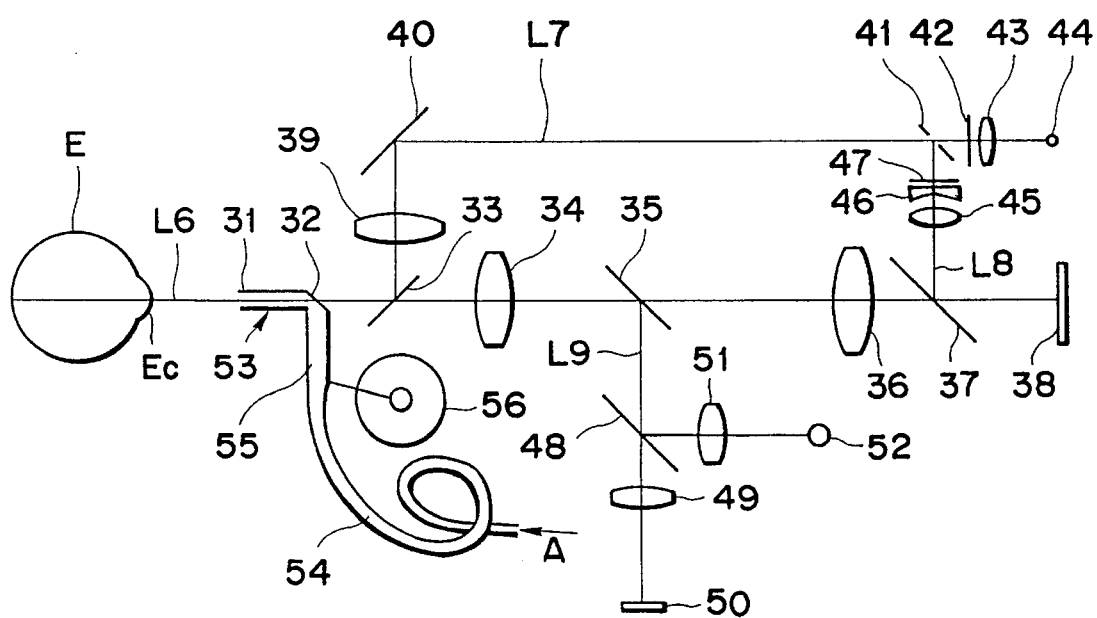
FIG. 2 is a schematic view showing the arrangement of the second embodiment of the present invention.

FIG. 2 is a schematic view showing the arrangement of the second embodiment of the present invention, which is a combination of a tonometer and an eye refractometer. In an optical path L6 in front of an eye E to be examined, a nozzle 31, a window member 32, a dichroic mirror 33, an objective lens 34, a dichroic mirror 35, a lens 36, a dichroic mirror 37, and an imaging device 38 are arranged.

In an optical path L7 along the incident direction of the dichroic mirror 33, a lens 39, a mirror 40, a perforated mirror 41, a central aperture stop 42 conjugated to the pupil of the eye E, a lens 43, and a light source 44 are arranged. In an optical path L8 between the dichroic mirror 37 and the perforated mirror 41, a lens 45, a separation prism 46 consisting of six wedge prisms, and a 6-hole aperture 47 are interposed. In an optical path L9 along the reflection direction of the dichroic mirror 35, a half mirror 48, a lens 49, and a photodetector 50 are disposed. A lens 51 and a measurement light source 52 are placed in the incident direction of the half mirror 48.

In this embodiment, as pressurizing means, a chamber type unit is used instead of a cylinder type unit. That is, air A from a chamber (not shown) is sprayed from the nozzle 31 through a flexible tube 54 and a fluid passage 55. The fluid applying unit 53 is pivoted by a solenoid 56 so that the unit can be inserted into or removed from the optical path L6.

In order to use this embodiment having the above arrangement as a tonometer, a light beam from the measurement light source 52 is projected onto a cornea Ec of the eye E to be examined via the lens 51, the half mirror 48, the dichroic mirror 35, the objective lens 34, the dichroic mirror 33, the window member 32, and the nozzle 31. The reflected light passes around the nozzle 31 and is reflected by the dichroic mirror 35 through the objective lens 34. This reflected light is received by the photodetector 50. In this case, an intraocular pressure measuring method is similar to that of the first embodiment.

On the other hand, in order to use this embodiment as an eye refractometer, the solenoid 56 is powered to remove the fluid applying unit 53 from the optical path L6. However, the fluid applying unit 53 may be left on the optical path L6 in observing the anterior eye of the eye E to be examined by using the imaging device 38 for an alignment purpose. In this case, the anterior eye is imaged on the imaging device 38 through the objective lens 34 and the lens 36. When the light source 44 is turned on with the pressurizing measurement unit 53 being removed from the optical path L6, the resultant infrared light beam projects a spot light beam onto an eye fundus Er via the lens 43, the central aperture stop 42, the perforated mirror 41, the mirror 40, the lens 39, and the dichroic mirror 33 on the optical path L7. The light reflected by the eye fundus Er returns through the same optical path L7 and is reflected by the perforated mirror 41. This reflected light is again reflected by the dichroic mirror 37 through the 6-hole aperture 47, the separation prism 46, and the lens 45, thereby forming six spot images on the imaging device 38. The eye refraction is obtained by calculating the positions of these light beams by using an arithmetic means (not shown) in accordance with a known method.

Figure 3:
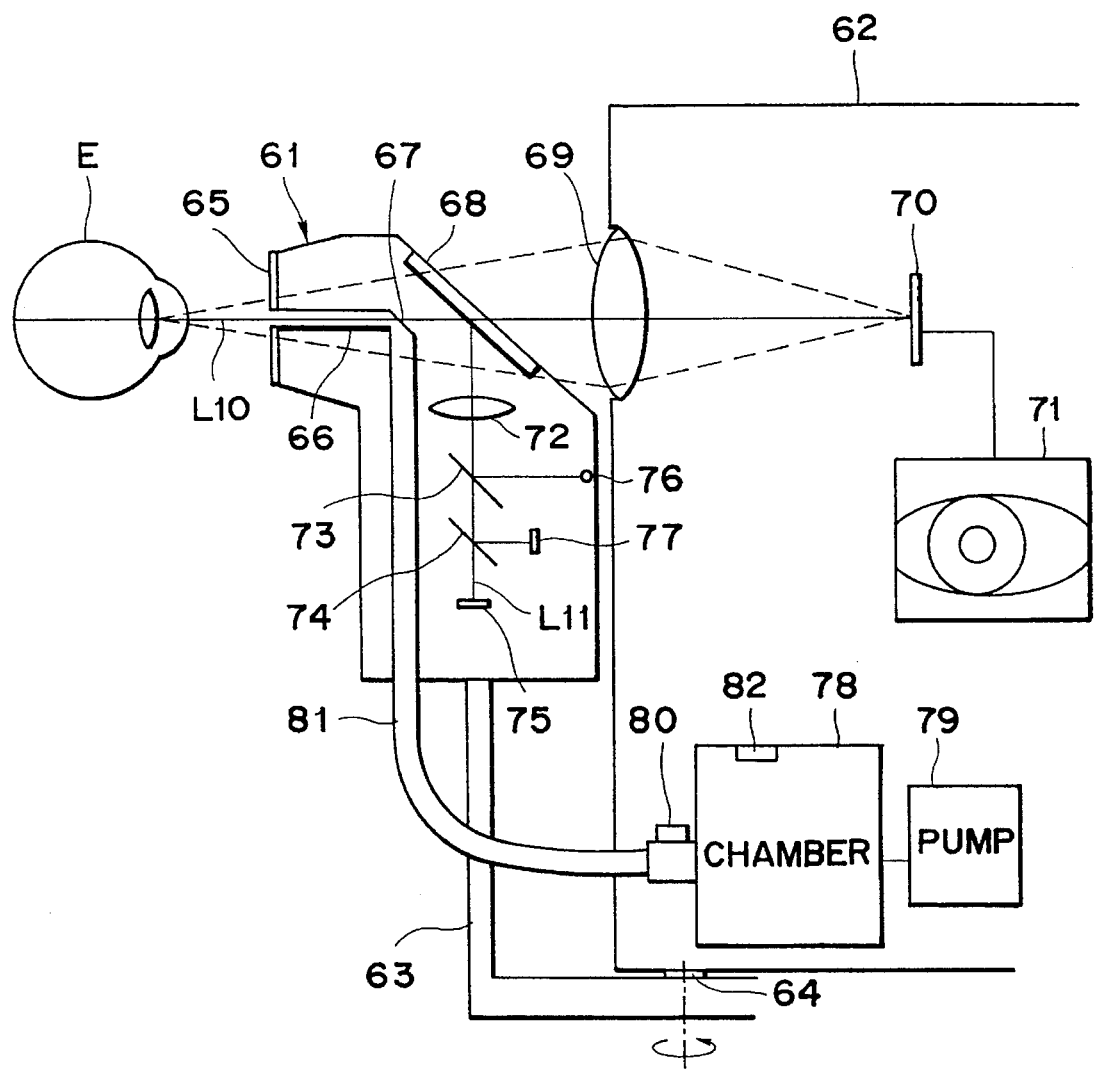
FIG. 3 is a schematic view showing the arrangement of the third embodiment of the present invention.

FIG. 3 is a schematic view showing the arrangement of the third embodiment of the present invention, which is a combination of a tonometer and an eye refractometer, as in the second embodiment. In this third embodiment, an intraocular pressure measurement optical system and a pressurizing measurement system are in part housed in a head 61, and the head 61 itself can be inserted into or removed from an optical path. That is, the head 61 is supported by an eye refractometer 62 via an arm 63 and manually or electrically pivoted about a shaft 64.

In an optical path L10 in front of an eye E to be examined, a transparent member 65, a nozzle 66, a window member 67, a beam-splitting member 68, an objective lens 69, and a CCD 70 are arranged, and the output of the CCD 70 is connected to a television monitor 71. Note that the objective lens 69, the CCD 70, and the television monitor 71 are provided in the eye refractometer 62, and other components are mounted on the head 61. In an optical path L11 inside the head 61 along the reflection direction of the beam-splitting member 68, a lens 72, half mirrors 73 and 74, and a photodetector 75 are arranged. In addition, a measurement light source 76 and a photodetector 77 are disposed in the reflection directions of the half mirrors 73 and 74, respectively.

A chamber 78 for spraying air against the eye E to be examined is also provided in the eye refractometer 62. Air in the chamber 78, which is compressed by a pump 79, is sprayed from the nozzle 66 through a flexible tube 81 upon opening of an electromagnetic valve 80. Note that a pressure sensor 82 for measuring an intraocular pressure is arranged inside the chamber 78.

In order to use this embodiment with the above arrangement as a tonometer, a light beam from the light source 76 is reflected by the beam-splitting member 68 through the half mirror 73 and the lens 72 and irradiates a cornea Ec of the eye E to be examined through the window member 67 and the nozzle 66. Light reflected by the cornea Ec passes through the transparent member 65 and the beam-splitting member 68 and is received by the CCD 70 through the objective lens 69. The image of an anterior eye formed on the CCD 70 is displayed on the television monitor 71 and used in alignment.

The light beam reflected by the beam-splitting member 68 is incident on the photodetector 75 through the lens 72 and the half mirrors 73 and 74 and used in measurement of an intraocular pressure. This method of measuring an intraocular pressure is exactly the same as the first embodiment. That is, the light beam reflected by the beam-splitting member 68 is again reflected by the half mirror 74 and incident on the photodetector 77. When the cornea Ec is located at a predetermined position, the peak output is obtained. By spraying air against the cornea Ec at this moment, the cornea Ec deforms to change its curvature by a predetermined amount. The output is maximized when the image of the light source 76 and the photodetector 75 become conjugate to each other. The pressure in the chamber 78 at the instant this maximum output is obtained is detected by the pressure sensor 82, and the detected value is converted to an intraocular pressure.

In order to use this embodiment as an eye refractometer, the entire head 61 is removed from the optical path L10 by pivoting it about the shaft 64, and measurement is performed by using a known eye refraction measurement system (not shown) arranged as a branch of the optical path from the objective lens 69 in the eye refractometer 62. Note that the light source 76 in the head 61 may partially emit visible light so that the light source can also be used as a fixation sight lamp, or an internal eye guide mark of the eye refractometer 62 may be used for this purpose. In addition, an enlargement lens system can be used instead of the television monitor 71. In this embodiment, the moving part of the apparatus for combining the individual ophthalmic apparatuses consists only of the mechanism for inserting/removing the head 61 in the left-and-right direction. Therefore, the overall structure is simple and is not large in size.

Figure 4:
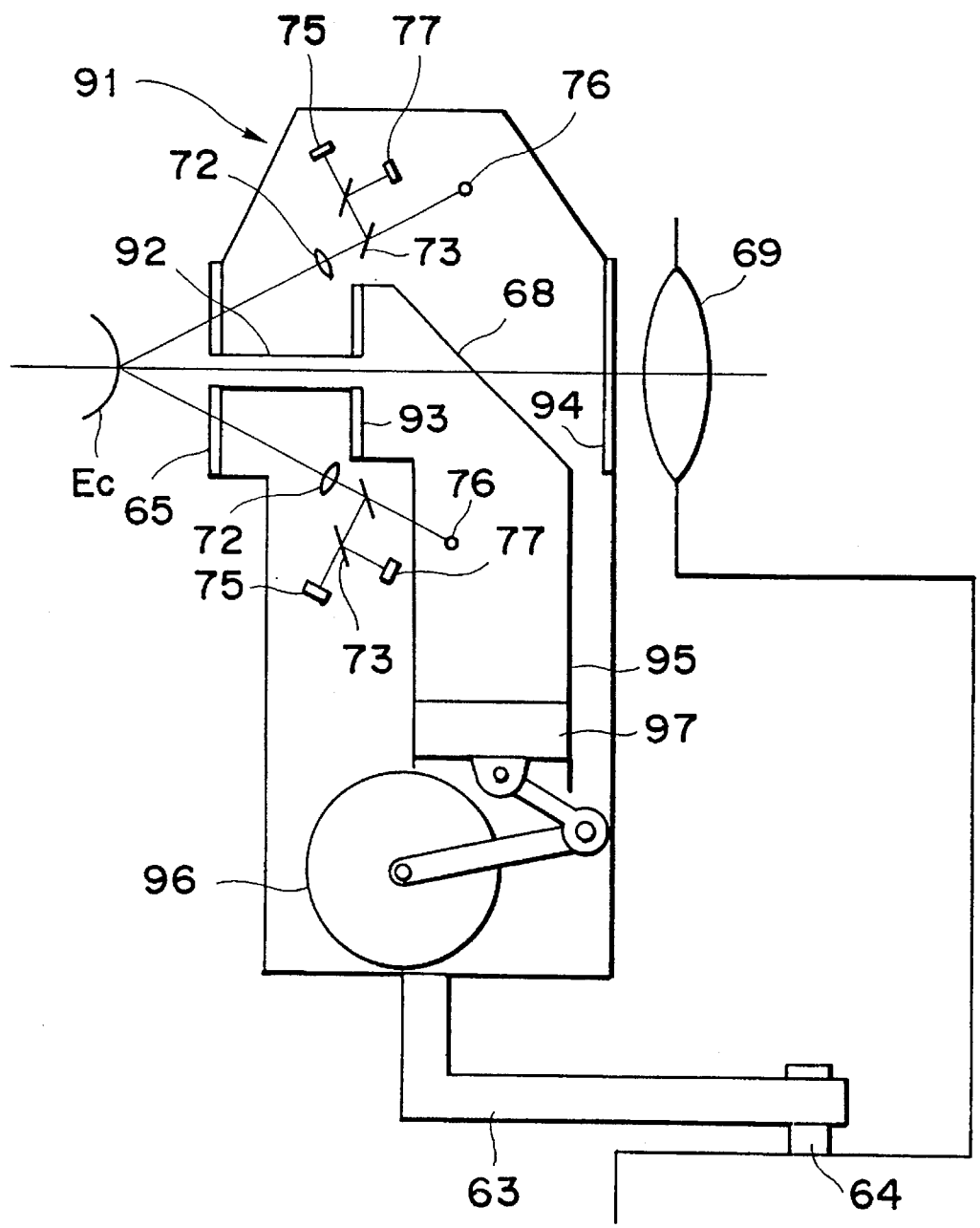
FIG. 4 is a schematic view showing the arrangement of the fourth embodiment of the present invention.

FIG. 4 is a schematic view showing the arrangement of the fourth embodiment of the present invention, in which the same reference numerals as in FIG. 3 denote the same parts. In this fourth embodiment, the intraocular pressure measurement optical system and the pressurizing system in the third embodiment are entirely housed in a head 91. Two optical systems for intraocular pressure measurement similar to that of the third embodiment are arranged symmetrically about a nozzle 92. A transparent member 65, an optical holding member 93, a window member 68, and a window member 94 are arranged on the optical axis of the head 91 to allow passing of a light beam. Air in a cylinder 95 is compressed by a piston 97 interlocked with a solenoid 96, and is sprayed from the nozzle 92 against a cornea Ec.

In order to use this embodiment with the above arrangement as a tonometer, light beams from light sources 76 pass through half mirrors 73 and formed into parallel light beams by lenses 72. These parallel light beams are projected onto the cornea Ec, and the reflected light beams propagate through optical paths opposite to their respective incident optical paths and are received by photodetectors 75. A method of measuring an intraocular pressure is generally similar to that of the third embodiment described above with reference to FIG. 3. The use of this embodiment as an eye refractometer is also the same as the third embodiment, and effects similar to those of the third embodiment can be obtained.

Figure 5:
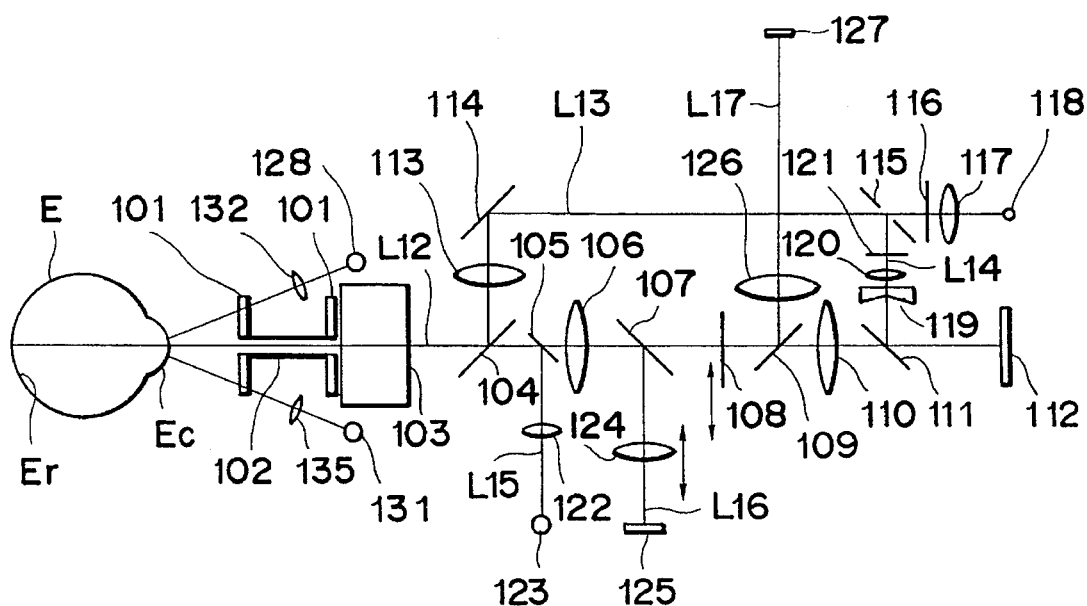
FIG. 5 is a plan view showing the arrangement of the fifth embodiment of the present invention.
Figure 6:
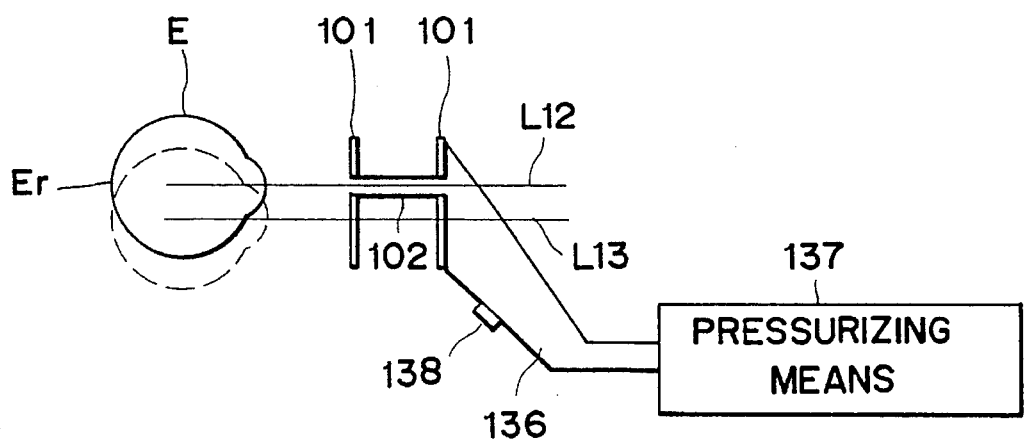
FIG. 6 is a side view showing a pressurizing measuring means.

FIG. 5 is a plan view showing the arrangement of a composite apparatus of a tonometer, an eye refractometer, and a cornea curvature meter, according to the fifth embodiment of the present invention. FIGS. 6 and 7 are side and front views, respectively, of the apparatus. This fifth embodiment is different from the above embodiments in that the tonometer and the eye refractometer are arranged such that the levels of their optical axes differ from each other. In an optical path L12 in front of an eye E to be examined, a nozzle 102 held by transparent optical holding members 101, a window member 103, a dichroic mirror 104, a half mirror 105, a lens 106, a dichroic mirror 107, an aperture 108, a dichroic mirror 109, a lens 110, a dichroic mirror 111, and an imaging device 112 are arranged. Note that the aperture 108 can be inserted in a position of the back focal point of the lens 106 in measurement of a cornea curvature, as indicated by arrows in FIG. 5.

In an optical path L13 along the reflection direction of the dichroic mirror 104, a lens 113, a mirror 114, a perforated mirror 115, a central aperture stop 116, a lens 117, and a light source 118 are disposed. In an optical path L14 between the dichroic mirror 111 and the perforated mirror 115, a separation prism 119 consisting of six wedge prisms, a lens 120, and a 6-hole aperture 121 are interposed. In an optical path L15 along the incident direction of the half mirror 105, a lens 122 and a light source 123 are placed. In an optical path L16 along the reflection direction of the dichroic mirror 107, a lens 124 movable in the direction of optical axis and a visual target 125 are arranged. A lens 126 and a photodetector 127 are disposed in an optical path L17 along the reflection direction of the dichroic mirror 109. In addition, around the optical axis near the eye E to be examined, light sources 128 to 131 and collimator lenses 132 to 135 for measurement of a cornea curvature are arranged.

As shown in FIG. 6, a pressurizing means 137 is coupled via a chamber 136 to the nozzle 102 for applying air to a cornea Ec of the eye E to be examined, and a pressure sensor 138 is provided in the chamber 136. As is also apparent from FIG. 6, the optical path L12 used in the application as a tonometer and the optical path L13 used in the application as an eye refractometer are arranged at different levels.

This embodiment with the above arrangement is used as a tonometer in the same manner as the above embodiments. That is, a light beam emitted from the light source 123 for intraocular pressure measurement is projected onto the cornea Ec of the eye E to be examined through the lens 122, the half mirror 105, the dichroic mirror 104, the window member 103, and the nozzle 102. At this time, by applying air to the cornea Ec from the pressurizing means 137 through the nozzle 102, the curvature of the cornea Ec changes. The reflected image of the light source 123 obtained by corneal reflex becomes conjugate to the photodetector 127 through the optical holding members 101, and the output from the photodetector 127 is maximized. The pressure in the chamber 136 at this time is measured by the pressure sensor 138, thereby obtaining an intraocular pressure.

In order to use this embodiment as an eye refractometer, a vertical moving mechanism (not shown) is moved upward together with the nozzle 102 to align the optical path L13 for eye refraction measurement with the visual axis of the eye E to be examined. In this condition, a light beam emitted from the light source 118 for eye refraction measurement projects a spot light beam onto an eye fundus Er through the lens 117, the central aperture stop 116, the perforated mirror 115, the mirror 114, the lens 113, the dichroic mirror 104, the window member 103, and the optical holding members 101. The reflected light beam returns through the same optical path L13 and is reflected by the perforated mirror 115. This reflected light is again reflected by the dichroic mirror 111 through the peripheral 6-hole aperture 121, the lens 120, and the separation prism 119, so that six reflected light beams are incident on the imaging device 112. The positions of these light beams are calculated by an arithmetic means (not shown) to obtain the value of eye refraction. Note that in this eye refraction measurement, the lens 124 is moved as indicated by an arrow to change the diopter of the visual target 125.

The imaging device 112 can display, for a positioning purpose, the anterior part of the eye E to be examined on a television monitor 139 by using the lenses 106 and 110, as shown in FIGS. 8A and 8B. In this case, alignment marks 140 and 141 of the tonometer and the eye refractometer, respectively, can be electrically synthesized on the television monitor 139. In this embodiment, since the levels of the optical axes of the tonometer and the eye refractometer are different from each other as shown in FIGS. 8A and 8B, it is more efficient to set the screen of the television monitor 139 such that its longitudinal direction is vertical.

In order to use this embodiment in the measurement of a cornea curvature, the aperture 108 is inserted at the back focal point of the lens 106, thereby focusing four images 128' to 131', formed on the cornea Ec by the four light sources 128 to 131 and the four corresponding collimator lenses 132 to 135, onto the imaging device 112 through the lenses 106 and 110, as shown in FIG. 8C. In this case, another alignment mark 142 is displayed on the monitor, and the curvature of the cornea Ec is calculated from the positional relationship between the images 128' to 131' by using an arithmetic means (not shown) in accordance with a well-known method.

In this embodiment, since the optical path is moved vertically, the light beam for eye refraction measurement is not interrupted by the nozzle 102. Therefore, the nozzle need not be removed for the eye refraction measurement.

Figure 9:
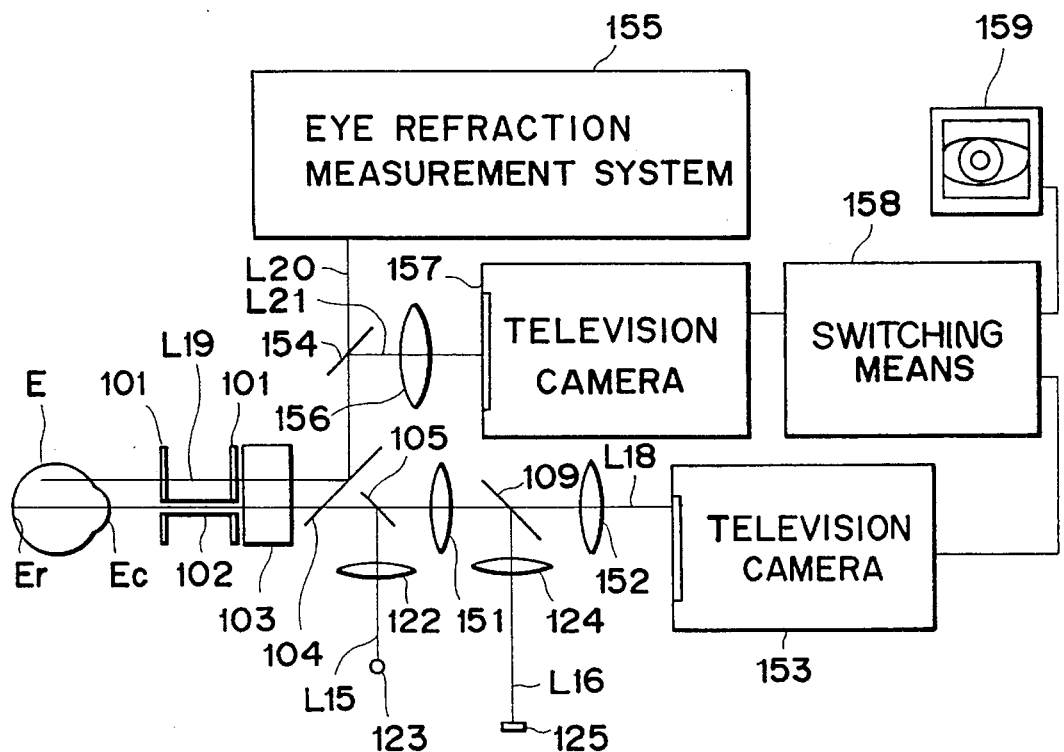
FIG. 9 is a schematic view showing the arrangement of the sixth embodiment of the present invention.

FIG. 9 is a plan view showing the arrangement of the sixth embodiment of the present invention. Note that the same reference numerals as in FIG. 5 denote parts having the same functions in FIG. 9. In this embodiment, an intraocular pressure measurement optical path L18 and an eye refraction measurement optical path L19 are located at different positions in the lateral direction. In the optical path L18 aligned with the visual axis of an eye E to be examined, a nozzle 102 held by optical holding members 101, a window member 103, a dichroic mirror 104, a half mirror 105, a lens 151, a dichroic mirror 109, a lens 152, and a television camera 153 are arranged. In the optical path L19 deviated from the optical path L18, the optical holding members 101, the window member 103, and the dichroic mirror 104 are arranged. In an optical path L20 along the reflection direction of the dichroic mirror 104, a dichroic mirror 154 and an eye refraction measurement system 155 are disposed. In addition, a lens 156 and a television camera 157 are placed in an optical path L21 in the reflection direction of the dichroic mirror 154. The outputs of the television cameras 153 and 157 are connected to a switching means 158, and the output of the switching means 158 is connected to a television monitor 159.

In order to switch measurement modes in the above arrangement, a sliding mechanism for positioning is used to adjust the optical path L18 or L19 to align with the visual axis of the eye E to be examined. The amount of this adjustment is very small, about 5 mm. Note that before the measurement, the respective alignment marks of the individual paths are electrically displayed at the center of the television monitor 159. In this embodiment, the moving part of the apparatus consists only of the sliding mechanism for positioning, and the apparatus requires no additional moving mechanism for combining the individual ophthalmic apparatuses, resulting in a simple structure.

Figure 10:
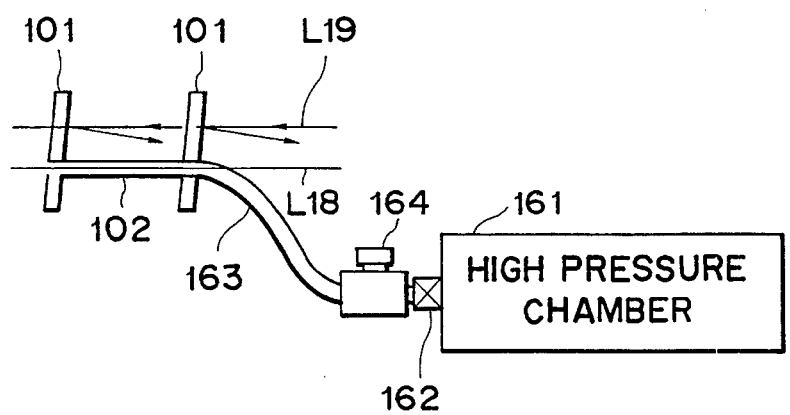
FIG. 10 is a schematic view showing the arrangement of a pressurizing measuring means according to the seventh embodiment of the present invention.

FIG. 10 is a schematic view showing the arrangement according to the seventh embodiment of the present invention, in which the same reference numerals as in the sixth embodiment shown in FIG. 9 denote the same parts. In this embodiment, optical holding members 101 consisting of a transparent material are set to be inclined with respect to an eye refraction measurement optical path L19, so that light reflected by the optical holding members 101 is not incident on an eye refraction measurement imaging device. Air for intraocular pressure measurement is supplied from a high-pressure chamber 161 to a flexible tube 163 via an electromagnetic valve 162 and sprayed from a nozzle 102. The corresponding intraocular pressure is measured by a pressure sensor 164. Also in this embodiment, the moving part of the apparatus consists only of a sliding mechanism for positioning, and no moving mechanism for combining the individual ophthalmic apparatuses is needed. Therefore, the structure of the entire apparatus is simple.

As described above, in the composite ophthalmic apparatus of any of the above embodiments, the structure of the moving part required for combining the individual eye examining apparatuses is not large. In addition, since it is possible to make use of a sliding mechanism or an observation mechanism originally provided, the mechanism is not complicated and the ease of operation is not degraded.

Figure 11:
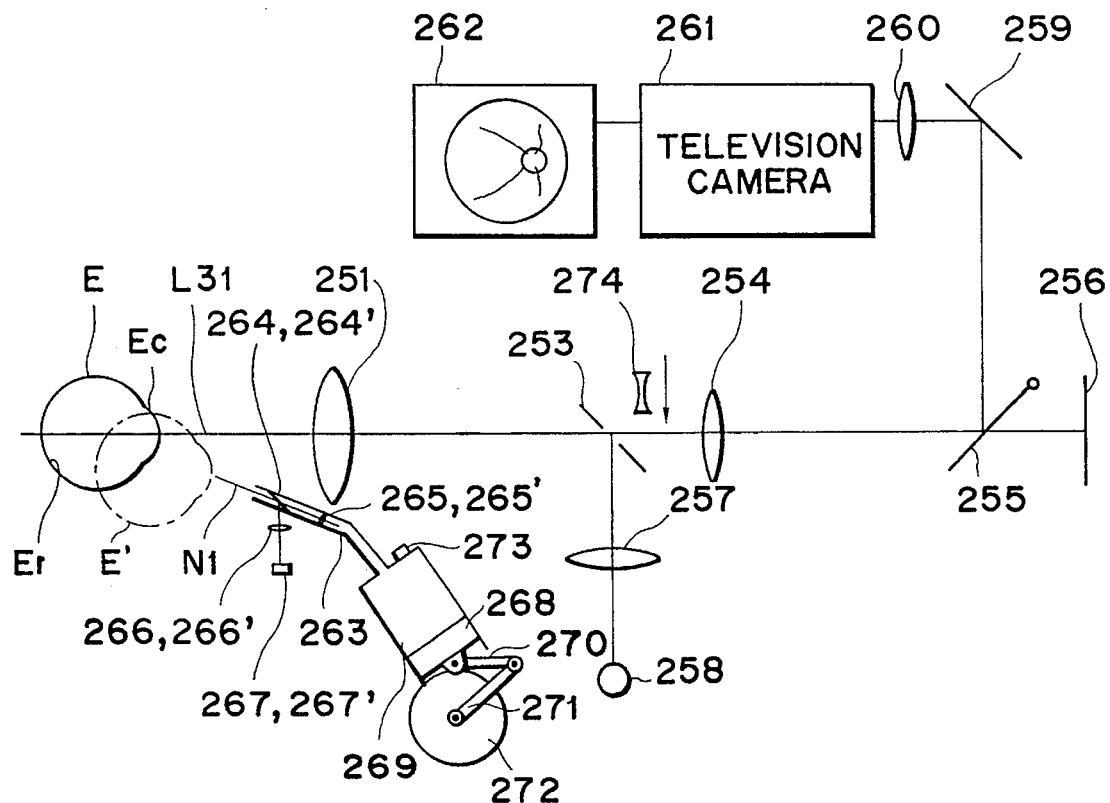
FIG. 11 is a front view showing the arrangement of the eighth embodiment of the present invention.
Figure 12:
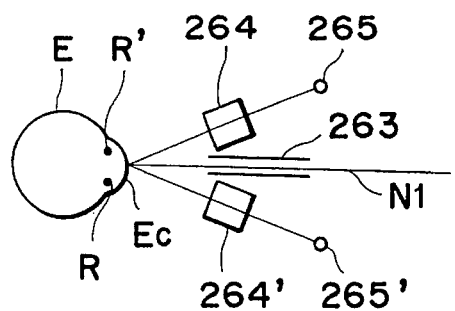
FIG. 12 is a plan view showing a main part of the eighth embodiment.

FIG. 11 is a side view showing the arrangement of a composite apparatus of a noncontact tonometer and an eye fundus camera according to the eighth embodiment of the present invention. FIG. 12 is a plan view showing a main part of the apparatus. In a visual axis L31 extending in front of an eye E to be examined, an objective lens 251, a perforated mirror 253, a lens 254, a quick return mirror 255, and a film 256 are arranged in this order. A lens 257 and a light source 258 for illuminating an eye fundus are arranged in the incident direction of the perforated mirror 253. A mirror 259 is disposed in the reflection direction of the quick return mirror 255, and a lens 260, a television camera 261 using infrared rays, and a television monitor 262 are disposed in the reflection direction of the mirror 259.

A nozzle 263 is placed in an air flow axis N1 obliquely extending downward from the eye E to be examined. In planes at the same level on the left and right sides of the nozzle 263, two measurement optical systems, i.e., half mirrors 264 and 264' and spot-like light sources 265 and 265' are arranged. Lenses 266 and 266' and photoelectric sensors 267 and 267' are arranged in the reflecting directions from the half mirrors 264 and 264', respectively. A cylinder 269 having a piston 268 fitted in it is connected to the nozzle 263, and the piston 268 is coupled to a solenoid 272 via a rod 270 and an arm 271. A pressure sensor 273 for measuring the inner pressure of the cylinder 269 is provided in a portion of the cylinder 269. A concave lens 274 is so arranged as to be inserted into or removed from a position between the perforated mirror 253 and the lens 254 on the visual axis L31. The concave lens 274 is used to observe the eye E' for positioning it. In addition, the television monitor 262 displays marks Pm and Pm', an alignment mark Am, and a fixed reference mark Sm.

In order to photograph an eye fundus Er in the above arrangement, a light beam emitted from the light source 258 is reflected by the perforated mirror 253 through the lens 257 and illuminates the eye fundus Er of the eye E to be examined through the objective lens 251. The image of the eye fundus is positioned by the television camera 261 and the television monitor 262 and recorded on the film 256 with the quick return mirror 255 removed from the visual axis L31.

Figure 13:
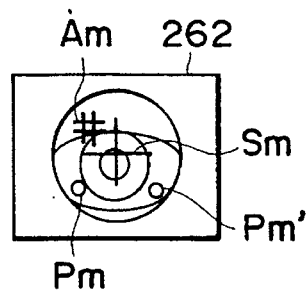
FIG. 13 is a view for explaining an anterior eye image displayed on a television monitor.
Figures 14A, 14B:
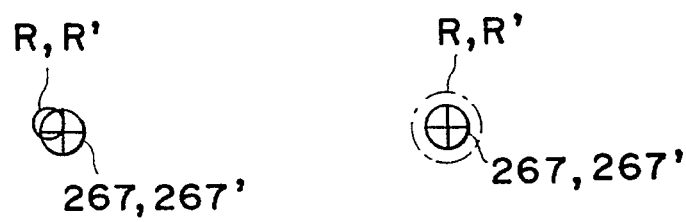
FIGS. 14A and 14B are views for explaining anterior eye images incident on a photoelectric sensor.

In order to measure an intraocular pressure, the apparatus is adjusted such that the eye E to be examined is located at a position E' indicated by an alternate long and short dashed line in FIG. 11 with respect to the apparatus. That is, the eye E to be examined is guided slightly downward by the use of the fixation sight lamp (not shown), and the concave lens 274 is inserted into the visual axis L31 to display an anterior eye on the television monitor 262 as shown in FIG. 13. With this arrangement, since the visual axis L31 and the air flow axis N1 are located in the same plane, light beams emitted from the spot-like light sources 265 and 265' are reflected by a cornea Ex through the half mirrors 264 and 264'. Reflected images R and R' of the cornea Ec are reflected by the half mirrors 264 and 264' and received by the photoelectric sensors 267 and 267' through the lenses 266 and 266'. As shown in FIGS. 14A and 14B, each of the photoelectric sensors 267 and 267' consists of a four-leaf element. FIG. 14A shows a condition in which the positions are slightly deviated from each other in a focused state, and FIG. 14B shows a condition in which the positions are aligned in a defocused state. That is, in the focused state, the sizes of the reflected images R and R' and the photoelectric sensors 267 and 267' become substantially the same; when the positions are aligned, the reflected images R and R' and the photoelectric sensors 267 and 267' overlap each other.

When the positions are aligned in the focused states of both the photoelectric sensors 267 and 267', the solenoid 272 is powered to drive the piston 268 to compress air in the cylinder 269, thereby spraying the air from the nozzle 263 against the cornea Ec. In this case, if the air is sprayed perpendicularly to the cornea Ec at a position below the apex of the cornea Ec, it is possible to obtain a measurement value similar to that obtained when air is sprayed against the apex of the cornea Ec. When the air is sprayed against the cornea Ec, the cornea Ec is deformed to reduce its curvature, so that the reflected images R and R' are set in defocused states. The moment the signal levels from the photoelectric sensors 267 and 267' decrease in this condition, the pressure in the cylinder 269 is measured by the pressure sensor 273, and the measurement value is converted to the intraocular pressure of the eye E'.

Note that in the alignment operation, the marks Pm and Pm' and the cornea reflected images R and R' are aligned first to perform positioning roughly, and then the fixed reference mark Sm and the alignment mark Am generated electrically on the basis of the signals from the photoelectric sensors 267 and 267' are aligned to perform more accurate positioning. This alignment mark Am is also used for focusing; the focusing is indicated by changing the interval of double lines. The fixation sight lamp (not shown) for use in intraocular pressure measurement guides the eye E to be examined to a position below the visual axis L31 and slightly above the air flow axis N1. In this embodiment, since the eye E to be examined and the nozzle 263 are located relatively distant from each other, no inconvenience occurs in manipulation of photographing the eye fundus Er.

Figure 15:
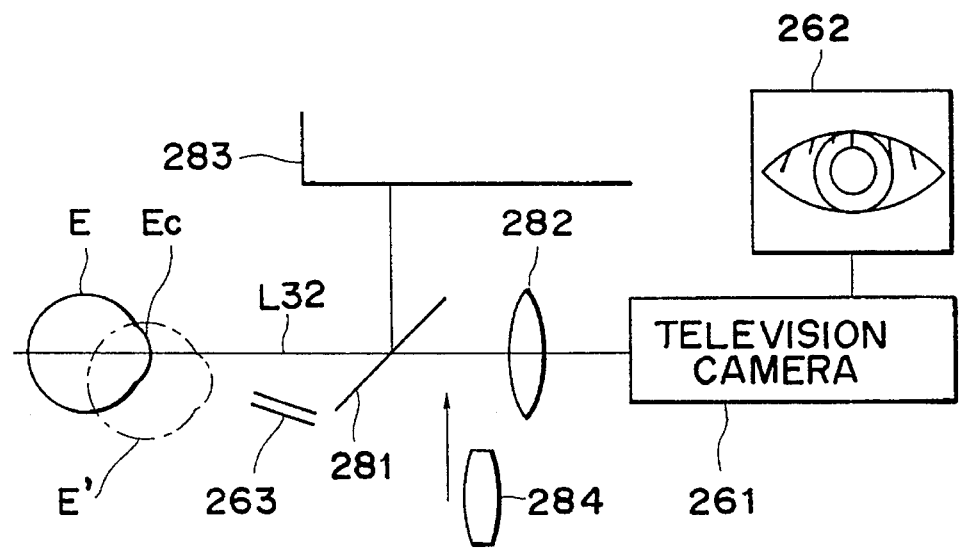
FIG. 15 is a front view showing the ninth embodiment of the present invention.
Figure 16:
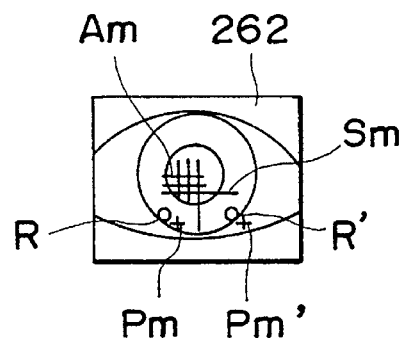
FIG. 16 is a view for explaining an anterior eye image displayed on a television monitor.

FIG. 15 is a front view showing the arrangement of a composite apparatus of a noncontact tonometer and an eye refractometer according to the ninth embodiment of the present invention. In this embodiment, a dichroic mirror 281 and a lens 282 are interposed on a visual axis L32 between an eye E to be examined and a television camera 261, and a measurement optical system 283 of an eye refractometer is arranged in the incident/reflection direction of the dichroic mirror 281. A lens 284 is so arranged as to be inserted into or removed from a position between the dichroic mirror 281 and the lens 282. The lens 284 enlarges an image displayed on a television monitor 262. Note that a pressurizing deformation system including a nozzle 263 and other arrangements are the same as those shown in FIG. 11. An image on the television monitor 262 shown in FIG. 15 indicates an anterior eye in the case of eye refraction measurement, and that shown in FIG. 16 indicates an enlarged anterior eye in the case of intraocular pressure measurement. Here again, the eye E to be examined is moved to a position E' indicated by an alternate long and short dashed line in FIG. 15 for intraocular pressure measurement, and an effect similar to that of the eighth embodiment can be obtained.

Figure 17:
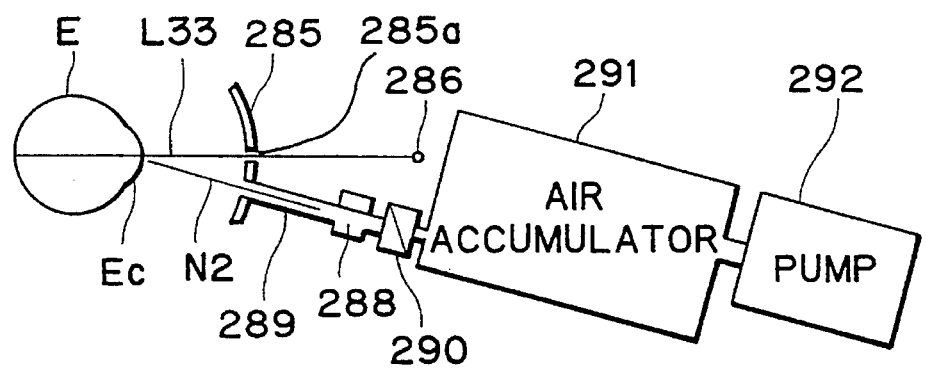
FIG. 17 is a side view showing the tenth embodiment of the present invention.
Figure 18:
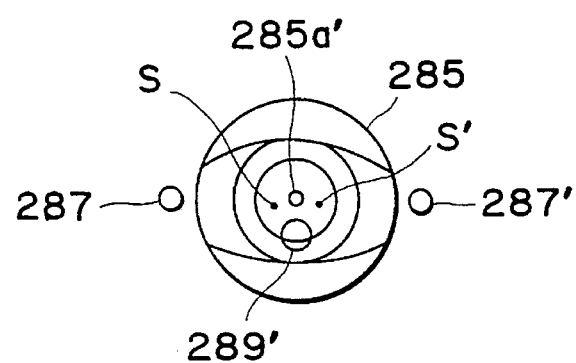
FIG. 18 is a view for explaining an anterior eye image formed on a perforated concave mirror.

FIG. 17 is a side view showing the arrangement of the tenth embodiment of the present invention. The tenth embodiment is a hand-held tonometer capable of measurement without requiring an examiner. A perforated concave mirror 285 having a hole 285a at its center and a fixation sight lamp 286 are arranged on a visual axis L33 in front of an eye E to be examined. Illumination light sources 287 and 287' are disposed on both sides of the perforated concave mirror 285, as shown in FIG. 18. A nozzle 289 having a pressure sensor 288 is arranged in an air flow axis N2 below the perforated concave mirror 285. An air accumulator 291 is coupled to the nozzle 289 via an electromagnetic valve 290, and a pump 292 is coupled to the air accumulator 291.

The eye E to be examined guided by the fixation sight lamp 286 through the hole 285a of the perforated concave mirror 285 is illuminated by the light sources 287 and 287', and cornea reflected images S and S' of these light sources are formed in an enlarged scale by the perforated concave mirror 285. Note that the hole 285a of the concave mirror 285 and the nozzle 289 are also shown. An object to be examined itself performs positioning such that the fixation sight lamp 286 is located in the middle of the reflected images S and S'. Air in the air accumulator 291 compressed by the pump 292 is sprayed from the nozzle 289 against a cornea Ec by opening the electromagnetic valve 290. The pressure at the instant the cornea Ec is deformed to a predetermined degree is measured by the pressure sensor 288 and converted to the intraocular pressure of the eye E. Also in this embodiment, the eye is aligned such that the air flow axis N2 becomes perpendicular to the cornea Ec, but comes across the cornea at a different point from the apex. Since no measurement optical system is placed in the direction of the air flow axis N2, the air accumulator 291 can be installed immediately after the nozzle 289. This makes it possible to reduce the volume of the air accumulator 291 and miniaturize the entire apparatus.

In each of the above embodiments, the air flow axis of a nozzle and the visual axis of another eye examining means are separated obliquely from each other. This facilitates the combination of individual ophthalmic apparatuses or miniaturization of the entire system without degrading the respective functions of the apparatuses.

Furthermore, although air is not sprayed against the top of a cornea, it is sprayed perpendicularly in the meridian direction of the cornea. Therefore, the cornea is deformed as when air spraying is performed against its top portion, and a measurement value similar to a value in that case can be obtained.

Figure 19:
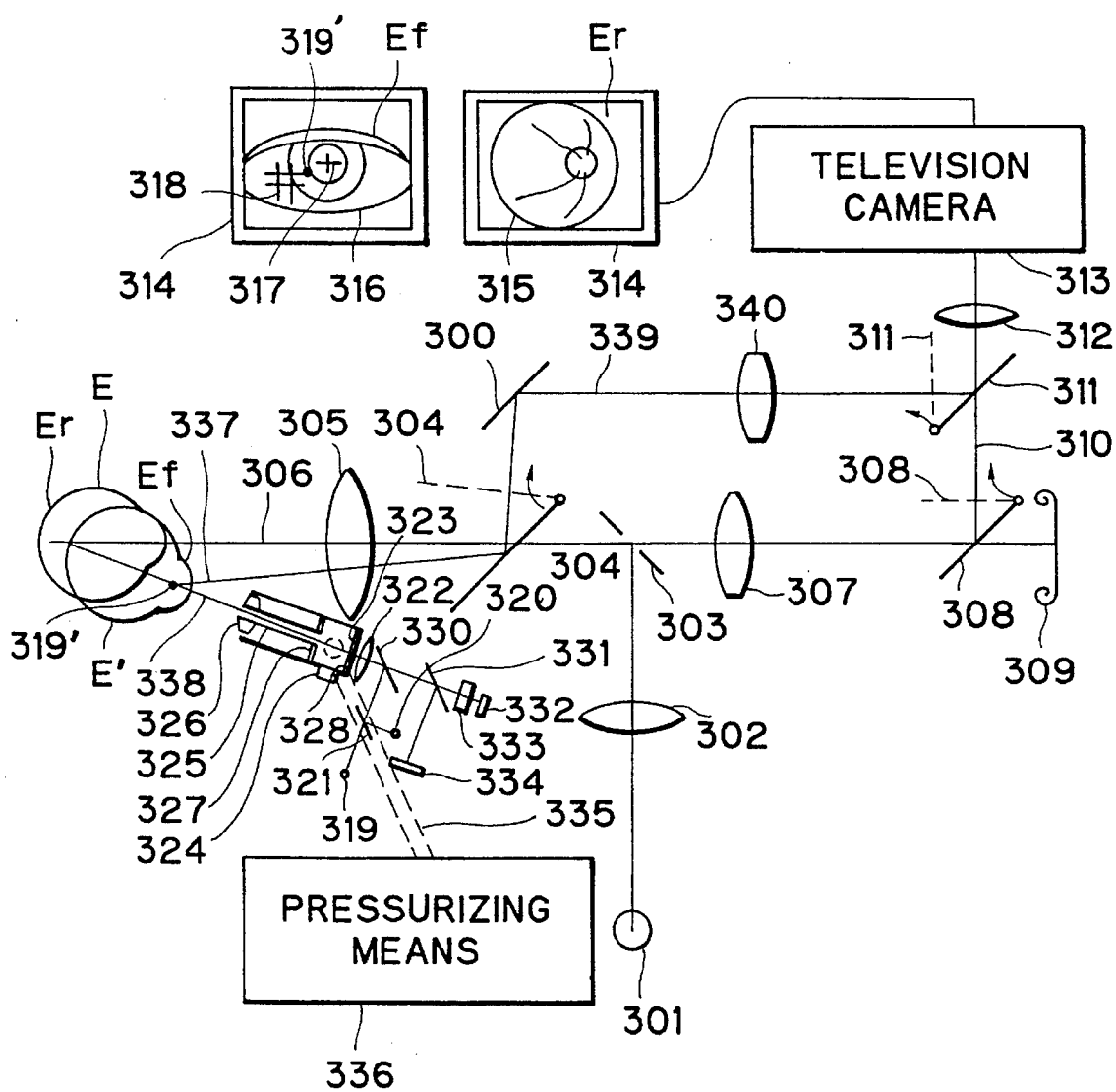
FIG. 19 is a schematic view for explaining the 11th embodiment of the present invention.

FIG. 19 is a schematic view showing the arrangement of an ophthalmological apparatus according to the 11th embodiment of the present invention. In an optical path 306 along the visual axis of an eye E to be examined, an objective lens 305, a movable mirror 304, a perforated mirror 303, an imaging lens 307, a quick return mirror 308, and a film 309 are arranged in this order from the eye to be examined. A mirror 300 and a lens 340 are arranged in an optical path 339 formed in the reflection direction of the movable mirror 304 when the movable mirror is set obliquely in the optical path 306. The optical path 339 is coupled to an optical path 310 via a movable mirror 311 similarly set obliquely in the optical path 339. In the optical path 310 formed in the reflection direction of the quick return mirror 308 when the quick return mirror 308 is inserted in the optical path 306, the movable mirror 311, a lens 312, and a television camera 313 are arranged, and an output from the television camera 313 is displayed, on a monitor 314. A lens 302 and a light source 301 for illuminating an eye fundus are arranged in the reflection direction of the perforated mirror 303.

The monitor 314 on the right-hand side indicates eye fundus imaging, and the monitor 314 on the left-hand side indicates anterior eye imaging. These illustrations contain an eye fundus image 315, an anterior eye image 316, a reference mark 317 formed electrically, an alignment mark 318, and a fixation sight light source image 319'.

A pressurizing measurement unit of a tonometer has a nozzle 325 provided on an air flow axis 338 extending obliquely downward from the eye E to be examined, and compressed air supplied from pressurizing means 336 is sprayed from the nozzle 325 through a tube 335. A pressure sensor 324 is arranged in a space formed between the tube 335 and the nozzle 325. In this unit, a perforated lens 326, a glass plate 327 for holding the nozzle, a window 323, a lens 322, half mirrors 330 and 331, a cylindrical lens 333, and a four-element sensor 332 are arranged in this order from the eye to be examined. A dichroic mirror 321 is disposed in the reflection direction of the half mirror 330. A measurement light source 319 and a fixation sight light source 320 are arranged in the transmission direction and the reflection direction, respectively, of the dichroic mirror 321. A sensor 334 is placed in the reflection direction of the half mirror 331.

In eye fundus photographing, a light beam from the light source 301 irradiates an eye fundus Er of the eye E to be examined via the lens 302, the perforated mirror 303, and the objective lens 305, thereby illuminating the eye fundus Er. In this case, the movable mirrors 304 and 311 are raised to positions indicated by broken lines. Light reflected by the eye fundus Er passes through the hole of the perforated mirror and is imaged by the infrared light television camera 313 via the lens 307, the quick return mirror 308, and the lens 312 to form the eye fundus image 315 on the monitor 314. In this condition, an examiner performs positioning and focusing between the eye to be examined and the apparatus in accordance with known techniques. After these operations, the examiner depresses a shutter button (not shown) to move the mirror 308 upward, thereby photographing the eye fundus image on the film 309.

In intraocular pressure measurement, the movable mirrors 304 and 311 are returned to the positions indicated by solid lines. At this time, light propagating through the optical path 339 forms the anterior eye image 316 of the eye to be examined on the monitor 314. The eye to be examined is directed downward as indicated by E' in order to view the fixation sight light source 320 seen in the nozzle 325, and the relative position of the eye to be examined with respect to the apparatus is moved a little toward the apparatus. In this case, the apparatus itself is moved toward the eye to be examined by a sliding table (not shown). In this condition, air is supplied from the pressurizing means 336 to the nozzle 325 through the tube 335. The air pressure before the air flows into the nozzle is monitored by the pressure sensor 324.

A light beam from the measurement light source 319 propagates via the dichroic mirror 321, the half mirror 330, the lens 322, and the window 323 and reaches a cornea Ef through the nozzle 325. Light reflected by the cornea propagates through the lens 326 and the glass plate 327 located outside the nozzle hole and is detected by the four-element sensor 332 via the window 323, the lens 322, the half mirrors 330 and 331, and the cylindrical lens 333. The four-element sensor 332 has the same arrangement as the sensor 267 shown in FIG. 14. A three-dimensional position of the eye to be examined with respect to the apparatus can be uniquely determined from a detected light quantity balance between individual elements constituting the four-element sensor 332 for detecting a light beam from the cylindrical lens. The obtained information concerning the position of the eye to be examined is displayed as the alignment mark 318 on the monitor via an arithmetic unit (not shown). An examiner controls the sliding table such that the alignment mark 318 overlaps the reference mark 317, thereby performing alignment between the apparatus and the eye to be examined. The alignment mark 318 represents a position in the direction of the optical path 306 by an interval between two cross marks and a position in the vertical direction by a distance from the mark 317, displaying the position of the eye to be examined three-dimensionally. The measurement direction is different from the direction of the optical path 306. Therefore, when the sliding table adjustable in both the horizontal and vertical directions is moved along the optical path 306 alone, only the interval between the cross marks constituting the mark 318 is changed, and the position of the mark is kept unchanged (although a detection value indicating the position of the eye to be examined in the direction perpendicular to the optical path 306 changes). When the marks 317 and 318 overlap each other to complete the alignment, air is automatically sprayed from the nozzle 325 to deform a cornea as described above under the control of an arithmetic unit (not shown).

Corneal reflex light reflected by the half mirror 331 is detected by the sensor 334. When the cornea reaches a predetermined deformation, the corneal reflex image of the light source 319 becomes conjugate to the sensor 334, and the peak output is obtained from the sensor 334. The predetermined deformation of the cornea is detected by detecting this peak output. The intraocular pressure of the eye to be examined can be obtained from a pressure detected by the pressure sensor 324 at this point, in accordance with a known technique.

In this embodiment, the arrangement may be altered such that observation of an anterior part of the eye eye can also be performed before photographing of an eye fundus image.

Figure 20:
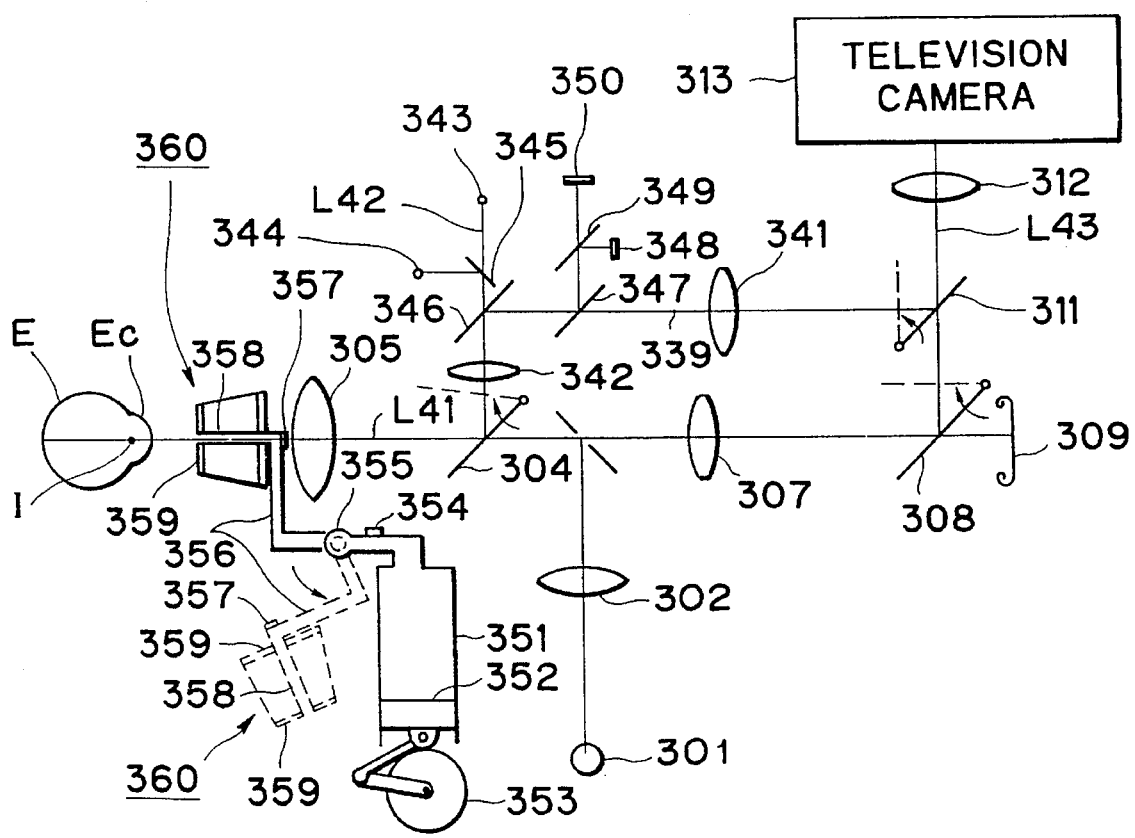
FIG. 20 is a schematic view for explaining the 12th embodiment of the present invention.

FIG. 20 is a schematic view showing the arrangement of an ophthalmological apparatus according to the 12th embodiment of the present invention. In an optical path L41 along the visual axis of an eye E to be examined, a nozzle 358 held by a glass plate 359, a window 357, an objective lens 305, a movable mirror 304, a perforated mirror 303, an imaging lens 307, a quick return mirror 308, and a film 309 are arranged in this order from the side of the eye E to be examined. In an optical path L42 formed in the reflection direction of the movable mirror 304 when the movable mirror 304 is set obliquely in the optical path L41, a lens 342, a half mirror 346, a dichroic mirror 345, and a measurement light source 343 are disposed. A fixation sight light source 344 is placed in the reflection direction of the dichroic mirror 345. In optical path L43 formed in the reflection direction of the quick return mirror 308 when the quick return mirror 308 is inserted in the optical path L41, a movable mirror 311, a lens 312, and the television camera 313 are arranged. An output from the television camera is displayed on a monitor similar to those of the above embodiments. A dichroic mirror 347 and a lens 341 are interposed in an optical path between the half mirror 346 and the movable mirror 311. A half mirror 349 is provided in the reflection direction of the dichroic mirror 347, and sensors 348 and 350 are arranged in the reflection direction and the transmission direction, respectively, of the half mirror 349. A lens 302 and a light source 301 for photographing are disposed in the reflection direction of the perforated mirror 303.

In an air applying unit 360 of a tonometer having a nozzle 358, a glass plate 359, and a window 357, air in a cylinder 351 is compressed by a piston 352 driven by a solenoid 353 and sprayed from the nozzle 358 through a tube 356. A pressure sensor 354 is provided for the tube 356 to constantly monitor the air pressure in the tube. The air applying unit 360 is manually or electrically pivoted about a pivot so as to be inserted into or removed from the optical path L41 in accordance with the intended use of the ophthalmological apparatus. In this embodiment, the position of the eye E to be examined in eye fundus photographing is kept unchanged from that in intraocular pressure measurement. That is, in eye fundus photographing, the pressurizing measurement unit 360 can be removed from the optical path L41 by pivoting it about a pivot 355.

In intraocular pressure measurement, the pressurizing measurement unit 360 is set at a position indicated by a solid line, and the movable mirrors 304 and 311 are also set at positions indicated by solid lines. In this case, an anterior eye image of the eye to be examined is displayed on the monitor by light propagating through an optical path 339. The eye E to be examined gazes at the fixation sight light source 344 seen in the nozzle 358. A light beam from the measurement light source 343 propagates via the dichroic mirror 345, the half mirror 346, the mirror 304, the objective lens 305, and the window 357 and reaches a cornea Ec of the eye to be examined through the nozzle 358. Light reflected by the cornea propagates in the optical path in the reverse direction through the glass plate 359. The light is reflected by the half mirror 346 and received by the sensors 348 and 350 via the dichroic mirror 347 and the half mirror 349. The sensor 348 is located at a position where the sensor becomes conjugate to a corneal reflex image of a cornea of an eye to be examined located at a regular position. When the corneal reflex image and the sensor 348 become conjugate to each other to maximize an output from the sensor 348, completion of alignment between the eye to be examined and the apparatus is detected. When the maximum output is obtained from the sensor 348, an arithmetic unit (not shown) automatically drives the solenoid 353 to spray air from the nozzle 358. The sensor 350 is located at a position where the sensor become conjugate to a corneal reflex image obtained when the cornea of an eye to be examined reaches a predetermined deformation. When an output from the sensor 350 is maximized, the predetermined deformation of a cornea is detected. On the basis of the output from the pressure sensor 354 upon detection, an intraocular pressure is calculated by an arithmetic means (not shown) in accordance with a known method. In eye fundus photographing, the air applying unit 360 and the movable mirrors 304 and 311 are returned to positions indicated by broken lines. A light beam from the light source 301 irradiates the eye fundus of the eye E to be examined via the lens 302, the perforated mirror 303, and the objective lens 305, thereby illuminating the eye fundus. Light reflected by the eye fundus propagates through the hole of the perforated mirror and is imaged by the infrared light television camera 313 via the lens 307, the quick return mirror 308, and the lens 312, displaying an eye fundus image on the monitor. In this condition, an examiner performs positioning and focusing between the eye to be examined and the apparatus in accordance with known techniques. After completion of these operations, the examiner depresses a shutter button (not shown) to move the mirror 308 upward, thereby photographing the eye fundus image on the film 309.

In this embodiment, a light beam from the measurement light source propagates through the nozzle 358. However, the light beam may propagate through the glass plate 359. For example, the arrangement is altered such that a light source image is formed at the focal point of the objective lens 305, and that a parallel light beam is radiated obliquely onto a cornea. A sensor is located at a position symmetrical about the optical axis with respect to a position where the light beam passes, or at a conjugate position with respect to the position. When a cornea becomes applanated under pressure, the detected light is maximized. Therefore, by detecting the light beam by the sensor upon this deformation, the deformation can be detected in accordance with the detection output from the sensor. A measurement light beam for alignment can also be transmitted through the glass plate.

The glass plate 359 is provided so as to make a subject or an examinee to be examined, comfortable; the plate can be omitted if it is not particularly required.

What is claimed is:

1. An ophthalmological apparatus comprising:
    an anterior eye observing system having an observation optical system for displaying an anterior part of an eye to be examined;
    an intraocular pressure measuring system, having a pressurizing system for spraying a fluid against the eye to be examined and a deformation detecting system for detecting deformation of the eye to be examined caused by said pressurizing system, for measuring an intraocular pressure of the eye to be examined in accordance with the detection result of said deformation detecting system, said pressurizing system having a nozzle for fluid spraying at a position opposite to the eye to be examined; and
    an eye examining system for examining the eye to be examined by performing an operation other than the measuring of the intraocular pressure by receiving light from the eye to be examined via an examination optical system, said examination optical system and said observation optical system having a common optical axis in at least an objective unit,
wherein said nozzle is arranged outside the common optical axis of said objective unit when eye examination is performed by said eye examining system.

2. An apparatus according to claim 1, wherein said eye examining system performs eye fundus photographing as the examination of the eye to be examined.

3. An apparatus according to claim 1, wherein said eye examining system performs measurement of an eye refraction as the examination of the eye to be examined.

4. An apparatus according to claim 1, wherein said nozzle is fixed at a position apart from the common optical axis of said objective unit so as to spray a fluid against the eye to be examined in a direction oblique to the common optical axis.

5. An apparatus according to claim 1, wherein said nozzle is fixed to said objective unit by a holding member, said holding member being set inclined with respect to the common optical axis of said objective unit.

6. An ophthalmological apparatus comprising:
    an anterior eye observing system having an observation optical system for displaying an anterior part of an eye to be examined;
    an eye examining system for executing an examination of the eye to be examined by receiving light from the eye to be examined via an examination optical system, said examination optical system and said observation optical system having a common optical axis in at least an objective unit; and
    an intraocular pressure measuring system, having a pressurizing system for spraying a fluid against the eye to be examined and a deformation detecting system for detecting deformation of the eye to be examined caused by said pressurizing system, for measuring an intraocular pressure of the eye to be examined in accordance with the detection result of said deformation detecting system, said pressurizing system having a nozzle for fluid spraying at a position opposite to the eye to be examined,
wherein said nozzle is arranged outside the common optical axis of said objective unit when eye examination is performed by said eye examining system,
wherein said nozzle is so arranged as to be inserted into or removed from the common optical axis of said objective unit.

7. An ophthalmological apparatus, comprising:
    an anterior eye observing system having an observation optical system for displaying an anterior part of an eye to be examined;
    an eye examining system for executing an examination of the eye to be examined by receiving light from the eye to be examined via an examination optical system, said examination optical system and said observation optical system having a common optical axis in at least an objective unit;
    an intraocular pressure measuring system, having a pressurizing system for spraying a fluid against the eye to be examined and a deformation detecting system for detecting deformation of the eye to be examined caused by said pressurizing system, for measuring an intraocular pressure of the eye to be examined in accordance with the detection result of said deformation detecting system, said pressurizing system having a nozzle for fluid spraying at a position opposite to the eye to be examined,
wherein said nozzle is arranged outside the common optical axis of said objective unit when eye examination is performed by said eye examining system; and
    a housing for containing said intraocular pressure measuring system, said housing being movable between the eye to be examined and said objective unit.

8. An ophthalmological apparatus comprising:
    an anterior eye observing system having an observation optical system for displaying an anterior part of an eye to be examined;
    an eye examining system for executing an examination of the eye to be examined by receiving light from the eye to be examined via an examination optical system, said examination optical system and said observation optical system having a common optical axis in at least an objective unit; and
    an intraocular pressure measuring system, having a pressurizing system for spraying a fluid against the eye to be examined and a deformation detecting system for detecting deformation of the eye to be examined caused by said pressurizing system, for measuring an intraocular pressure of the eye to be examined in accordance with the detection result of said deformation detecting system, said pressurizing system having a nozzle for fluid spraying at a position opposite to the eye to be examined, wherein said nozzle is arranged outside the common optical axis of said objective unit when eye examination is performed by said eye examining system, wherein said nozzle is fixed at a position apart from the common optical axis of said objective unit and at a position opposite to a top of a cornea of the eye to be examined when intraocular pressure measurement is performed by said intraocular pressure measuring system.

9. An ophthalmological apparatus, comprising:

an anterior eye observing system having an observation optical system for displaying an anterior part of an eye to be examined;

an eye examining system for executing an examination of the eye to be examined by receiving light from the eye to be examined via an examination optical system, said examination optical system and said observation optical system having a common optical axis in at least an objective unit; and an intraocular pressure measuring system, having a pressurizing system for spraying a fluid against the eye to be examined and a deformation detecting system for detecting deformation of the eye to be examined caused by said pressurizing system, for measuring an intraocular pressure of the eye to be examined in accordance with the detection result of said deformation detecting system, said pressurizing system having a nozzle for fluid spraying at a position opposite to the eye to be examined, wherein said nozzle is arranged outside the common optical axis of said objective unit when eye examination is performed by said eye examining system, wherein said examination optical system has a pivot mirror provided at a position farther from the eye to be examined than said objective unit so as to be inserted into or removed from said examination optical system, and said deformation detecting system detects deformation of the eye to be examined via said pivot mirror when said pivot mirror is inserted into said examination optical system.

10. An apparatus according to claim 9, wherein said anterior eye observing system displays an anterior eye via said pivot mirror when said pivot mirror is inserted into said examination optical system.

11. An ophthalmological apparatus comprising:

an intraocular pressure measuring system, having a pressurizing system for spraying a fluid against the eye to be examined and a deformation detecting system for photoelectrically detecting deformation of the eye to be examined caused by said pressurizing system, for measuring an intraocular pressure of the eye to be examined in accordance with the detection result of said deformation detecting system, said pressurizing system having a nozzle for fluid spraying at a position opposite to the eye to be examined, and an eye examining system for examining the eye to be examined by performing an operation other than the measuring of the intraocular pressure by receiving light from the eye to be examined via an examination optical system, wherein said nozzle sprays a fluid against the eye to be examined from a position apart from an optical axis of said examination optical system and in a direction oblique to the optical axis of said examination optical system and perpendicular to a cornea of the eye to be examined.

12. An apparatus according to claim 11, wherein said eye examining system performs eye fundus photographing as the examination of the eye to be examined.

13. An apparatus according to claim 11, wherein said eye examining system performs eye refraction measurement as the examination of the eye to be examined.

14. A tonometer comprising:

a pressurizing system for spraying a fluid against an eye to be examined; and a deformation detecting system for photoelectrically detecting deformation of the eye to be examined caused by said pressurizing system, an intraocular pressure of the eye to be examined being measured in accordance with the detection result of said deformation detecting system, wherein said pressurizing system has a nozzle for fluid spraying at a position opposite to the eye to be examined, said nozzle spraying a fluid against a position except at the top of a cornea of the eye to be examined in a direction substantially perpendicular to a cornea of the eye to be examined.

* * * * *

UNITED STATES PATENT AND TRADEMARK OFFICE
CERTIFICATE OF CORRECTION

PATENT NO. : 5,523,808  
DATED : June 4, 1996  
INVENTOR(S) : YOSHIMI KOHAYAKAWA It is certified that error appears in the above-indentified patent and that said Letters Patent is hereby corrected as shown below:

ON THE COVER PAGE: Item [56]:

References Cited

After "5,144,346   9/1992   Nakamura et al." insert
--FOREIGN PATENT DOCUMENTS
62-275432      11/1987      Japan--.

COLUMN 1

Line 15, "pressure, of the eye" should read --pressure of the eye,--.

Line 26, "enlarged" should read --large--.

COLUMN 13

Line 43, "eye" (second occurrence) should be deleted.

UNITED STATES PATENT AND TRADEMARK OFFICE
CERTIFICATE OF CORRECTION

PATENT NO. : 5,523,808
DATED : June 4, 1996
INVENTOR(S) : YOSHIMI KOHAYAKAWA

It is certified that error appears in the above-indentified patent and that said Letters Patent is hereby corrected as shown below:

COLUMN 15

Line 22, "examined," should read --examined--.

Signed and Sealed this

Fifth Day of November, 1996

Attest:

BRUCE LEHMAN

Attesting Officer        Commissioner of Patents and Trademarks